US011690558B2

(12) United States Patent
Roberts et al.

(10) Patent No.: US 11,690,558 B2
(45) Date of Patent: *Jul. 4, 2023

(54) SURGICAL NAVIGATION WITH STEREOVISION AND ASSOCIATED METHODS

(71) Applicant: The Trustees of Dartmouth College, Hanover, NH (US)

(72) Inventors: David W. Roberts, Lyme, NH (US); Keith D. Paulsen, Hanover, NH (US); Alexander Hartov, Enfield, NH (US); Songbai Ji, Hanover, NH (US); Xiaoyao Fan, Lebanon, NH (US)

(73) Assignee: The Trustees of Dartmouth College, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/486,839

(22) Filed: Sep. 27, 2021

(65) Prior Publication Data

US 2022/0007991 A1 Jan. 13, 2022

Related U.S. Application Data

(63) Continuation of application No. 16/785,882, filed on Feb. 10, 2020, now Pat. No. 11,129,562, which is a (Continued)

(51) Int. Cl.
*A61B 5/00* (2006.01)
*G06T 7/33* (2017.01)
(Continued)

(52) U.S. Cl.
CPC ............ *A61B 5/377* (2021.01); *A61B 5/0042* (2013.01); *A61B 5/0077* (2013.01);
(Continued)

(58) Field of Classification Search
CPC .................................................. A61B 5/377
See application file for complete search history.

(56) References Cited

U.S. PATENT DOCUMENTS 5,303,705 A * 4/1994 Nenov ................. G01R 33/563
600/410
5,381,236 A * 1/1995 Morgan ................. G01B 11/24
250/201.7
(Continued)

*Primary Examiner* — Irfan Habib
(74) *Attorney, Agent, or Firm* — Cozen O'Connor

(57) ABSTRACT

A surgical guidance system has two cameras to provide stereo image stream of a surgical field; and a stereo viewer. The system has a 3D surface extraction module that generates a first 3D model of the surgical field from the stereo image streams; a registration module for co-registering annotating data with the first 3D model; and a stereo image enhancer for graphically overlaying at least part of the annotating data onto the stereo image stream to form an enhanced stereo image stream for display, where the enhanced stereo stream enhances a surgeon's perception of the surgical field. The registration module has an alignment refiner to adjust registration of the annotating data with the 3D model based upon matching of features within the 3D model and features within the annotating data; and in an embodiment, a deformation modeler to deform the annotating data based upon a determined tissue deformation.

18 Claims, 11 Drawing Sheets

Related U.S. Application Data continuation of application No. 15/367,243, filed on Dec. 2, 2016, now Pat. No. 10,568,535, which is a continuation-in-part of application No. PCT/US2015/033672, filed on Jun. 2, 2015, and a continuation-in-part of application No. 12/994,044, filed on Jan. 21, 2011, now Pat. No. 9,052,384, which is a continuation-in-part of application No. 14/373,443, filed on Jul. 21, 2014, now abandoned, which is a continuation-in-part of application No. 14/345,029, filed on Mar. 14, 2014, now Pat. No. 9,655,545, and a continuation-in-part of application No. PCT/US2013/024400, filed as application No. PCT/US2013/022266 on Jan. 18, 2013, said application No. PCT/US2015/033672 is a continuation-in-part of application No. PCT/US2013/020352, filed on Jan. 4, 2013, said application No. PCT/US2013/024400 is a continuation-in-part of application No. PCT/US2013/020352, filed as application No. PCT/US2012/055755 on Sep. 17, 2012.

(60) Provisional application No. 62/006,786, filed on Jun. 2, 2014, provisional application No. 61/594,862, filed on Feb. 3, 2012, provisional application No. 61/588,708, filed on Jan. 20, 2012, provisional application No. 61/583,092, filed on Jan. 4, 2012, provisional application No. 61/535,201, filed on Sep. 15, 2011.

(51) Int. Cl.
*A61B 34/10* (2016.01)
*A61B 5/377* (2021.01)
*G06T 3/00* (2006.01)
*H04N 13/257* (2018.01)
*H04N 13/239* (2018.01)
*A61B 90/00* (2016.01)
*A61B 5/055* (2006.01)
*A61B 5/369* (2021.01)

(52) U.S. Cl.
CPC .............. *G06T 3/0068* (2013.01); *G06T 7/33* (2017.01); *H04N 13/239* (2018.05); *H04N 13/257* (2018.05); *A61B 5/055* (2013.01); *A61B 5/369* (2021.01); *A61B 2034/104* (2016.02); *A61B 2034/105* (2016.02); *A61B 2034/107* (2016.02); *A61B 2090/367* (2016.02); *G06T 2207/10012* (2013.01); *G06T 2207/10064* (2013.01); *G06T 2207/10072* (2013.01); *G06T 2207/30016* (2013.01)

(56) References Cited

U.S. PATENT DOCUMENTS

| | | | | |
|---|---|---|---|---|
| 6,961,405 | B2 * | 11/2005 | Scherch | A61N 5/1049 378/65 |
| 9,167,222 | B2 * | 10/2015 | Park | H04N 13/178 |
| 9,330,477 | B2 * | 5/2016 | Rappel | G16H 40/63 |
| 9,655,545 | B2 * | 5/2017 | Ji | A61B 90/20 |
| 9,699,438 | B2 * | 7/2017 | Walsh | H04N 13/156 |
| 9,712,746 | B2 * | 7/2017 | Arcas | H04N 23/698 |
| 9,766,441 | B2 * | 9/2017 | Rappel | H04N 13/156 |
| 2007/0236514 | A1 * | 10/2007 | Agusanto | G06T 19/006 345/646 |
| 2009/0312611 | A1 * | 12/2009 | Mangiardi | A61B 17/3421 600/210 |
| 2010/0208963 | A1 * | 8/2010 | Kruecker | G06T 3/0081 382/131 |
| 2010/0231593 | A1 * | 9/2010 | Zhou | G06T 3/4007 345/428 |
| 2011/0128352 | A1 * | 6/2011 | Higgins | A61B 5/415 348/46 |
| 2014/0063241 | A1 * | 3/2014 | Li | G06T 7/001 348/143 |
| 2014/0362186 | A1 * | 12/2014 | Ji | G01C 11/02 348/46 |
| 2014/0378843 | A1 * | 12/2014 | Valdes | G02B 21/36 600/476 |

\* cited by examiner

ANNOTATING DATA 108

| | |
|---|---|
| RECORDED HYPERSPECTRAL IMAGE STREAM 502<br><br>REF 503 | RECORDED FLUORESCENCE IMAGE STREAM 504<br><br>REF 505 |
| RECORDED HYPERSPECTRAL MODEL 506<br><br>REF 507 | RECORDED FLUORESCENCE MODEL 508<br><br>REF 509 |
| RECORDED STEREO IMAGE STREAM 510<br><br>REF 511 | RECORDED 3D MODEL 512<br><br>REF 513 |
| MRI DATA 514<br><br>REF 515 | fMRI IMAGE 516<br><br>REF 517 |
| CT IMAGE 518<br><br>REF 519 | SPECT IMAGE 520<br><br>REF 521 |
| PET IMAGE 522<br><br>REF 523 | EEG DATA SET 524<br><br>REF 525 |
| EVOKED POTENTIALS DATA SET 526<br><br>REF 527 | MEG DATA SET 528<br><br>REF 529 |

*FIG. 5*

SURGICAL NAVIGATION WITH STEREOVISION AND ASSOCIATED METHODS

PRIORITY CLAIM & RELATED APPLICATIONS

This application is a continuation of U.S. patent application Ser. No. 16/785,882, filed Feb. 10, 2020, which is a continuation of U.S. patent application Ser. No. 15/367,243, filed Dec. 2, 2016, now U.S. Pat. No. 10,568,535, which is a continuation-in-part of International Patent Application No. PCT/US15/33672 filed Jun. 2, 2015, which claims priority to U.S. Provisional Patent Application No. 62/006,786 filed Jun. 2, 2014, the disclosures of which are incorporated herein by reference.

International Patent Application No. PCT/US15/33672 is also a continuation-in-part of U.S. patent application Ser. No. 12/994,044 filed on Jan. 21, 2011, now U.S. Pat. No. 9,052,384 issued Jun. 9, 2015, which is a National Stage Entry of PCT Patent Application Serial Number PCT/US2009/045082 filed May 22, 2009, which claims priority to U.S. Provisional Patent Application No. 61/055,355, filed May 22, 2008, the disclosure of which are incorporated herein by reference.

International Patent Application No. PCT/US15/33672 is also a continuation-in-part of International Patent Application No. PCT/US2013/020352 filed Jan. 4, 2013, which claims priority to U.S. Patent Application No. 61/583,092, filed Jan. 4, 2012, the disclosures of which are incorporated herein by reference.

International Patent Application No. PCT/US15/33672; is also a continuation-in-part of International Patent Application No. PCT/US2013/024400 filed Feb. 1, 2013, which claims priority to U.S. Provisional Patent Application No. 61/594,862 filed Feb. 3, 2012 and which is also a continuation-in-part of PCT Application No. PCT/US2013/020352 filed Jan. 4, 2013, which claims priority to U.S. Patent Application Ser. No. 61/583,092, filed Jan. 4, 2012. The disclosures of the above-referenced applications are each incorporated in their entirety herein by reference.

International Patent Application No. PCT/US15/33672 is related to U.S. patent application Ser. No. 13/145,505, filed in the United States Patent and Trademark Office on Jul. 20, 2011, now U.S. Pat. No. 8,948,851 issued Feb. 3, 2015, which is a United States National Phase application of International Patent Application No. PCT/US2009/066839 filed Dec. 4, 2009, which claims priority to U.S. Provisional Patent Application No. 61/145,900 filed Jan. 20, 2009. The disclosures of the above-referenced applications are each incorporated in their entirety herein by reference.

International Patent Application No. PCT/US15/33672 is also a continuation-in-part of U.S. application Ser. No. 14/373,443 filed Jul. 21, 2014 which is a National Stage Entry of PCT Application No. PCT/US2013/022266 filed Jan. 18, 2013, which claims priority to U.S. Provisional Application Ser. No. 61/588,708, filed Jan. 20, 2012. The disclosures of the above-referenced applications are each incorporated in their entirety herein by reference.

International Patent Application No. PCT/US15/33672 is also a continuation-in-part of U.S. patent application Ser. No. 14/345,029 filed Mar. 14, 2014, now U.S. Pat. No. 9,655,545, which is a national phase of PCT Application No. PCT/US2012/055755 filed Sep. 17, 2012, which in turn claims priority to U.S. Patent Application Ser. No. 61/535,201 filed Sep. 15, 2011. The disclosures of the above-referenced applications are each incorporated in their entirety herein by reference.

GOVERNMENT RIGHTS

This invention was made with government support under grant numbers R01 CA159324-01, R01 EB002082-11 and 1R21 NS078607 awarded by the National Institutes of Health. The United States Government has certain rights in the invention.

SUMMARY

A system for generating a photographic image of a surgical field, includes a stereo image capture device for capturing a stereo image stream from two cameras imaging the surgical field; and a stereo viewer for displaying the stereo image stream to a surgeon. The system also includes a stereo image to 3D surface extraction module, implemented as machine readable instructions stored in memory of a computer, that is capable of, when the instructions are executed by a processor of the computer, generating a first 3D model of the surgical field from the stereo image streams; a registration module, implemented as machine readable instructions stored in the memory, that is capable of, when the instructions are executed by the processor, co-registering annotating data with the first 3D model; and a stereo image enhancer, implemented as machine readable instructions stored in the memory, that is capable of, when the instructions are executed by the processor, graphically overlaying at least part of the annotating data onto the stereo image stream to form an enhanced stereo image stream for display by the stereo viewer, wherein the enhanced stereo stream enhances the surgeon's perception of the surgical field.

In another embodiment, a system configured for graphically representing and displaying a first and second annotating data in relation to a surgical field, including an interactive display device; a registration module, implemented as machine readable instruction stored in a memory of a computer, that is capable of, when the instructions are executed by a processor of the computer, co-registering the first and second annotating data; and a stereo image enhancer, implemented as machine readable instruction stored in the memory, that is capable of, when the instructions are executed by the processor, graphically overlaying at least part of the annotating data onto the stereo image stream to form an enhanced stereo image stream for display by the stereo viewer, wherein the enhanced stereo stream enhances the surgeon's perception of the surgical field.

In another embodiment, a method for surgical navigation with stereo vision, including capturing a stereo image pair of a surgical field; generating a 3D surface model from the stereo image pair; registering preoperatively captured annotating data with the 3D surface model; generating an enhanced stereo image based upon the stereo image pair and the annotating data; wherein the annotating data is graphically overlaid onto the stereo image pair.

BRIEF DESCRIPTION OF THE FIGURES

FIG. 5 shows examples of the annotating data of FIG. 1.

DETAILED DESCRIPTION OF THE EMBODIMENTS

Figure 1:
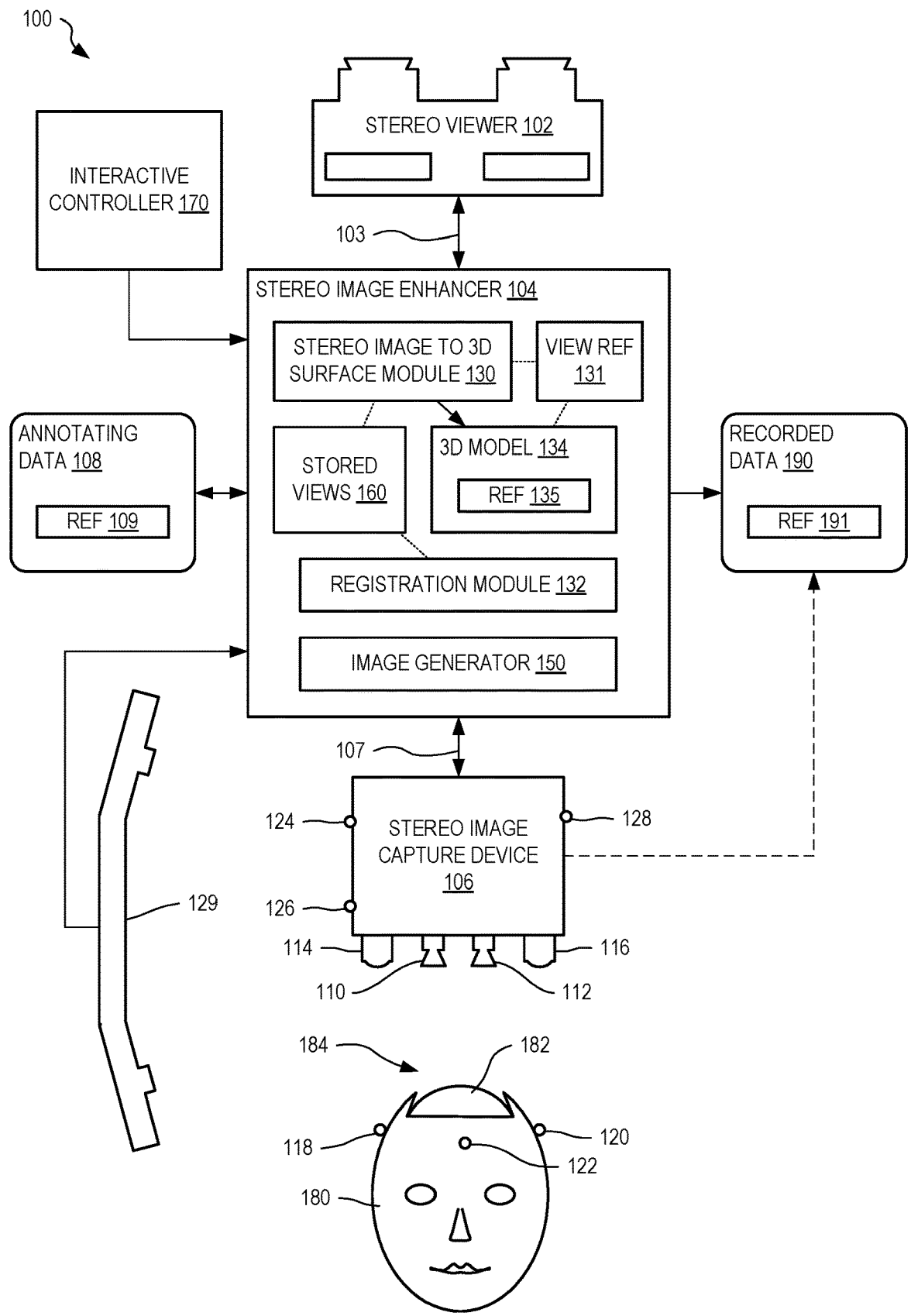
FIG. 1 shows one exemplary system for surgical navigation with stereovision, in an embodiment.

FIG. 1 shows one exemplary system 100 for surgical navigation with stereovision. System 100 includes a stereo viewer 102, a stereo image annotator or enhancer 104, and a stereo image capture device 106. System 100 is used to aid a surgeon during an operation on a person 180. In the example of FIG. 1, the surgeon is performing a procedure on a brain 182 of person 180. However, system 100 may be used to aid procedures on other parts of a person's body, and may be used when performing procedures on animals as well as on humans.

Stereo image capture device 106 includes illumination sources 114, 116 and at least two cameras 110, 112, that cooperate to capture a high quality stereo image stream 107 of a surgical field 184 (i.e., the area where the procedure is performed). System 100 may be calibrated using one or more calibration targets used in surgical field 184, as taught by PCT/US2009/045082.

Stereo image enhancer 104 receives stereo image stream 107 from capture device 106 and generates an enhanced stereo image stream 103 from stereo image stream 107 by adding information from annotating data 108. Annotating data 108 is for example a previously stored imaging data set such as one of (a) preoperative, intraoperative and postoperative radiological studies selected from the group including MRI, fMRI, CT, SPECT, and PET, and (b) physiological studies selected from the group including EEG, evoked potentials, and magnetoencephalography (MEG).

At least three reference points 118, 120, 122 may be attached to patient 180 for the duration of the procedure and the location of each reference point is defined as a location within a patent-centered coordinate system of patient 180. A tracker 129 determines, relative to itself, locations of reference points 118, 120, 122 attached to patient 180 and reference points 124, 126, 128 attached to stereo image capture device 106. Registration module 132 uses these locations to determine a view reference 131 (e.g., spatial relationship including relative position and orientation) between patient 180 and stereo image capture device 106. View reference 131 defines a spatial relationship of stereo image stream 107 relative to surgical field 184, and may also incorporate functions (e.g., zoom) of optics within cameras 110 and 112. Tracker 129 is in some embodiments a commercially available operating room tracking device that determines positions of reference points or transponders attached to equipment in the operating room, including stereo image capture device 106, and may include transponders attached to the patient. Tracker 129 may utilize one or both of optical and electromagnetic tracking as known in the art. In an alternate embodiment, where stereo image stream 107 includes images of reference points 118, 120, and 122, registration module 132 may automatically determine a spatial relationship between stereo image capture device 106 and patient 180, or to a frame attached to patent 180. 3D model 134 allows each pixel within stereo image stream 107 to be located within the patient-centered coordinate system. By determining this relationship between pixels of stereo image stream 107 and the patient-centered reference system, image post-processing techniques may be used to evaluate captured images.

In a particular embodiment where registration module 132 automatically determines spatial relationship between stereo image capture device and patient 180, the registration module determines features of patient bone structure from pre-operative CT scans and/or MRI scans, and registers this bone structure to features of bone structure determined from other CT scans and MRI scans for the same patient as well as to bone structure determined from 3D surfaces extracted from the stereo images. In the event an inconsistency, such as a scan with significant bony differences from other scans associated with the patient, or features of facial 3D surfaces that are inconsistent with features of bone structure extracted from the 3D surfaces, is found while automatically registering scans, a warning message is generated and provided to the surgeon.

It should be noted that stereo image stream 107 is recorded throughout a surgical procedure, and the recorded stereo image stream is effectively continuously geotagged by attaching an encoded position and orientation of image capture device 106 as determined by tracker 129 in real-time. The recorded image stream is available for documentation, and image pairs from the image stream are sampled and processed as indicated herein for extraction of 3D surface models and for co-registration of, and co-presentation of, data from other image sources, as described herein, periodically throughout a surgical procedure.

Stereo image enhancer 104 may be controlled, in a particular embodiment by the surgeon or a surgical assistant, to graphically enhance stereo image stream 107 with selected information from annotating data 108 such that the surgeon has an enhanced view of surgical field 184 through stereo viewer 102. Enhancer 104 includes a stereo image to 3D surface module 130 that generates a 3D model 134 of surgical field 184 from stereo image stream 107. 3D model 134 includes a reference 135 that defines a spatial relationship of 3D model 134 relative to the patient-centered coordinate system of patient 180, in a particular embodiment the spatial relationship is determined from tracker 129 based upon reference points 118, 120, 122. Although the patient-centered coordinate system described herein, other coordinate system may be used without departing from the scope hereof. For example, an operating-room centered coordinate system may be used, wherein the determined spatial relationship between patient 180 and stereo capture device 106 allows conversion of coordinates from one coordinate system to another according to a calibration.

Registration module 132 operates to co-register annotating data 108 (based upon a reference 109 associated, or included with, annotating data 108) and 3D model 134 (based upon determined reference 135) and generate graphical information from annotating data 108 that corresponds to surgical field 184 as imaged within image stream 107. For example, where annotating data 108 is a tomographic image generated from a MRI scan, that image may be scaled and oriented with respect to the surgical field viewed by the surgeon through stereo viewer 102 and graphically added to enhanced stereo image stream 103. Enhancer 104 thereby enhances the view of surgical field 184 seen by the surgeon by adding information from other sources and co-registering this information to a conventional optical view; thus the surgeon assimilates the information without the need to move or avert his/her eyes from the surgical field. In another embodiment, the surgeon may view a corresponding view of 3D model 134 and a 3D model of annotating data 108, and may view data from the 3D model 134 with superimposed annotating data 108 as rendered stereo images, as wireframe models, as one or more tomographic slices, as false-color renderings embodying color-encoded depth, as a combination of these representations.

Applicant notes that not only may the coordinate systems used to represent images from each modality may differ—for example an MRI may use a rectilinear coordinate system while an ultrasound imaging modality may use a polar coordinate system, but each series of images within a modality may be offset relative to other images of that modality=for example two successive MRIs may be offset relative to each other. A mapping between raw image coordinates and patient coordinates is established and, and images transformed from raw coordinate systems into the patient centered coordinate system, by registration module 132 for each image.

Registration module 132 may identify features within stereo image stream 107 and/or 3D model 134 that correspond to features identified within annotating data 108, wherein registration module 130 automatically aligns graphical images generated from annotating data 108 with stereo image stream 107. This automatic alignment may include one or more of shifting, rotating, warping, and scaling of annotating data 108 to align corresponding features between annotating data 108 and stereo image stream 107. Registration module 132 may also identify tissue shift within 3D model 134 as compared to annotating data 108, wherein registration module 132 may shift, rotate, warp, and/or scale annotating data 108 to correspond to 3D model 134. Brain, and many other organs, are soft, deformable, tissues. For example, when prepared for surgery, soft tissue may move as a result of skull removal, retraction, incision, and the like. Similarly, during surgery, tissue and inclusions therein such as tumors or critical structures may shift position. Stereo image to 3D surface module 130 continually updates 3D model 134 based upon stereo image stream 107 and registration module 132 continually compares 3D module 134 to annotating data 108, shifting, rotating, warping, and/or scaling annotating data 108 to match 3D model 134. In one embodiment, registration module 132 utilizes a mechanical model of tissue, instruments, and structure within surgical field 184 such that accurate manipulation of annotating data 108 may be made corresponding to detected movement within 3D model 134.

In one embodiment, where enhanced data 108 does not include imagery (i.e., EEG and/or evoked potentials), enhancer 104 generates contour lines mapped to 3D model 134 and corresponded to information within enhanced data 108.

In another embodiment, where enhanced data 108 includes a 3D model or data derived in a voxel-based form (e.g., MRI data), enhancer 104 may generate one or more cross sections through an indicated incision plane and map that cross section to the incision plane within 3D model 134 such that the surgeon views the corresponding 3D structures beneath the incision plane prior to, and after, making the actual incision. By displaying structure that is not readily or directly visible, the surgeon is made aware of such structures and their relative positions without the need to look away from the surgical field to reference other sources that may distract the surgeon from the procedure, or which may not represent current positions of the structures. That is, system 100 makes information of enhanced data 108 available within the same field of view as surgical field 184, thereby lessening need for the surgeon to look away from stereo viewer 102 or from surgical field 184.

System 100 includes an interactive controller 170 adapted to select one of a plurality of predefined stored views 160 of 3D model 134 and annotating data 108. In one embodiment, controller 170 is controlled by a surgeon's foot. In another embodiment, controller 170 is controlled by the surgeon's eye movement, wherein controller 170 may be implemented within stereo viewer 102. In yet another embodiment, controller 170 is controlled by a surgeon's voice using a trained speech interpretation interface. Stored views 160 define a plurality of views that combine annotating data 108 with stereo image stream 107 to generate enhanced stereo image stream 103. For example, one view may select a particular annotating data 108 for enhancing stereo image stream 103. Each view within stored views 160 also defines which portions of annotating data 108 to select for combining with stereo image stream 107. For example, where a surgical incision is planned (see planned surgical procedures 760 of FIG. 7), stored view 160 may define a view that graphically indicates planned incisions within enhanced stereo image stream 103, and may further define a corresponding portion of annotating data 3D model 222 for display with the planned incision to indicate tissue structures beneath the intended point of incision. This provides the surgeon with additional information relative to the next immediate step in the planned operational procedure.

Stored views 160 may also define an alternate viewing point for display within stereo viewer 102, wherein the stereo image enhancer 104 generates the alternate view based upon 3D model 134 and annotating data 108. For example, a surgeon may elect to temporarily view a side image of a patient's head to learn additional information from MRI tomography data stored within annotating data 108 in relation to surgical field 184.

Figure 2:
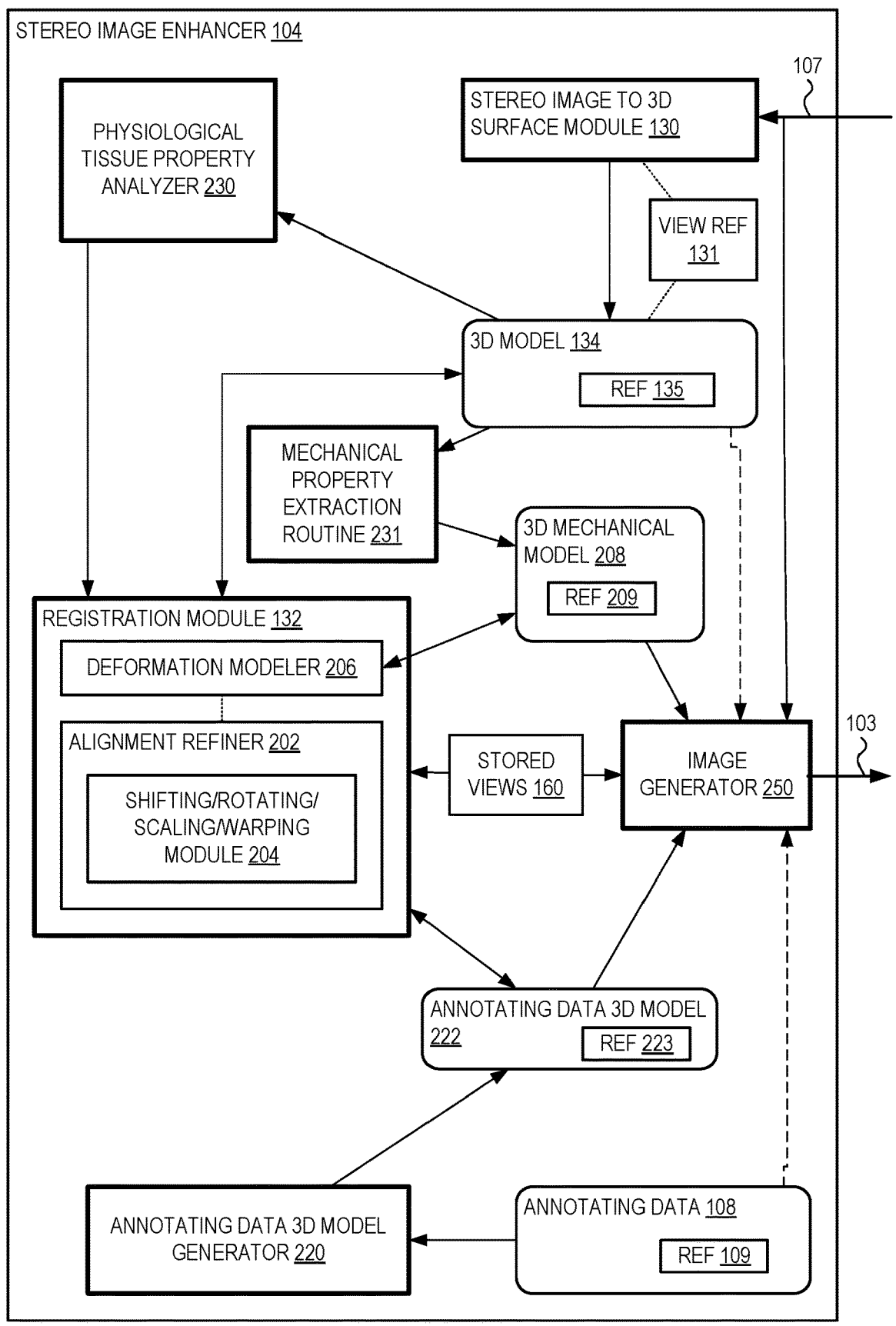
FIG. 2 shows the stereo image enhancer of FIG. 1 in further exemplary detail.

FIG. 2 shows stereo image enhancer 104 of FIG. 1 in further exemplary detail. Registration module 132 includes an alignment refiner 202 that utilizes a shifting/rotating/scaling/warping module 204 to improve registration of annotating data 108 with 3D model 134. Registration module 132 may also include a deformation modeler 206 that generates a 3D mechanical model 208 of annotating data 108 to model deformation of tissue within annotating data 108 based upon one or more of gravity, retraction, incision, and so on. Deformation modeler 206 thereby determines an appropriate deformation of annotating data 108 to match determined deformation of tissue within 3D model 134 and surgical field 184. In one example, a portion of a patient's skull is removed for surgery, resulting in reduced pressure and support for soft brain tissues. This reduced support allows the brain tissue to reposition as a result of gravity and reduced support. Deformation modeler 206 uses 3D mechanical model 208 to estimate such deformation and alignment refiner 202 uses shifting/rotating/scaling/warping module 204 to apply the estimated deformation to annotating data 108 such that annotating data 108 better aligns to 3D model 134. Similarly, when a surgeon applies retraction, or makes an incision, deformation modeler 206 uses 3D mechanical model 208 to estimate deformation of surrounding tissue to better align annotating data 108 to 3D model 134.

In one embodiment, 3D mechanical model 208 includes learning capability and is continually updated based upon detected deformation of actual tissue during the surgery. In an embodiment, stereo pairs captured using the stereo image capture device 106 are processed to extract a 3D surface model, which in turn is used to determine an actual surface configuration that is fed back to mechanical model 208; in a particular embodiment these 3D surface models are used to tune coefficients of a neural network implementation of a mechanical model 208. For example, each time 3D model 134 is updated based upon a performed surgical procedure, a mechanical property extraction routine 231 updates 3D mechanical model 208 to better predict the outcome of the procedure.

Stereo image enhancer 104 may also include an annotating data 3D model generator 220 that generates an annotating data 3D model 222 from annotating data 108. For example, where annotating data 108 represents an MRI scan, annotating data 3D model 222 is generated to represent a model of the scanned tissue. Where annotating data 108 represents data from a physiological study (i.e., physiological data) selected from the group including EEG, evoked potentials, and magnetoencephalography (MEG), annotating data 3D model generator 220 may generate annotating data 3D model 222 using contours based upon 3D model 134 or known shape of the patient.

Electrical activity may be recorded by EEG electrodes at particular times during a preoperative or an intraoperative EEG study, and may include recorded evoked potentials. Preoperative studies may use conventional scalp electrodes, while intraoperative studies may use any combination of scalp, cortical surface, and deep electrodes appropriate to the surgical procedure and stage of surgery at which EEG study is desired. This electrical activity is mapped onto a 3D model, for example as extracted from a CT scan or MRI imaging study, of the subject's brain. The resulting 3D maps of electrical activity are processed by annotating data 3D model generator 220 to generate annotating data 3D model 222 that is then co-registered with 3D model 134 extracted from stereo image stream 107. In this way, EEG activity associated with an epileptic focus may be used to enhance the surgeon's view of the surgical field. EEG activity associated with evoked potentials, such as potentials evoked when the subject speaks, may thus be added to the surgeon's view of the surgical field. For example, EEG activity associated with particular areas, such as Broca's area critical for speech, or visual cortex associated with the fovea, may be incorporated within enhanced stereo image stream 103.

Mechanical property extraction routine 231 updates 3D mechanical model 208 based upon observed displacement of tissue, such as when an indenter is place on the brain for example.

Stereo image enhancer 104 may also include a physiological tissue property analyzer 230 that processes intraoperative visual information for determination of tissue physiological properties, including but not limited to blood flow and oxygenation (oxygenation is determined by measuring tissue absorbance parameters at each of several wavelengths of light), light scattering and absorbance parameters, fluorescence of physiologic biomarkers, various chromophores including heme and porphyrins, and fluorescent optical biomarkers such as may be produced by metabolism of prodrugs. System 100 may have an integral tissue classifier based upon these physiological properties. For example, analyzer 230 may map and display tissue classifications and/or the presence or absence of particular degrees of oxygenation, light scattering, and absorbance parameters. Such physiological properties may be indicated within enhanced stereo image stream 103 and/or output separately. Since tumor cells may have different average sizes than normal cells, and many tumors are hypoxic, this information may be used to locate tumors.

Further, since patients may be conscious during surgery, blood flow and oxygenation is dependent upon neurological activity, and oxygenation is measured by the hyperspectral portion of the system by observing differences in absorption due to the spectral shift of hemoglobin with oxygenation, the system may perform intraoperative functional neuroimaging. Intraoperative functional neuroimaging is of use in isolating structures that require preservation, or in locating epileptic foci.

Registration module 132 may first align each model 134, 208, 222 and annotating data 108 based upon references 135, 209, 223, and 109 that defines a relationship of the model/data to a patient-centered reference system for example, and thereby to one another. Registration module 132 may then use alignment refiner 202 to better register two or more models together, such as by deforming annotating data 108 to align identifiable features within annotating data 108 with corresponding features within 3D model 134.

An image generator 250 then generates enhanced stereo image stream 103 based upon stereo image stream 107 and rendering of one or more of 3D model 134, 3D mechanical model 208, annotating data 3D model 222, and annotating data 108. For example, at least part of one or more of 3D model 134, 3D mechanical model 208, annotating data 3D model 222 and annotating data 108 may be graphically rendered and overlaid onto stereo image stream 107 to form enhanced stereo image stream 103.

Fluorescence/Hyperspectral Enhancement

Figure 3:
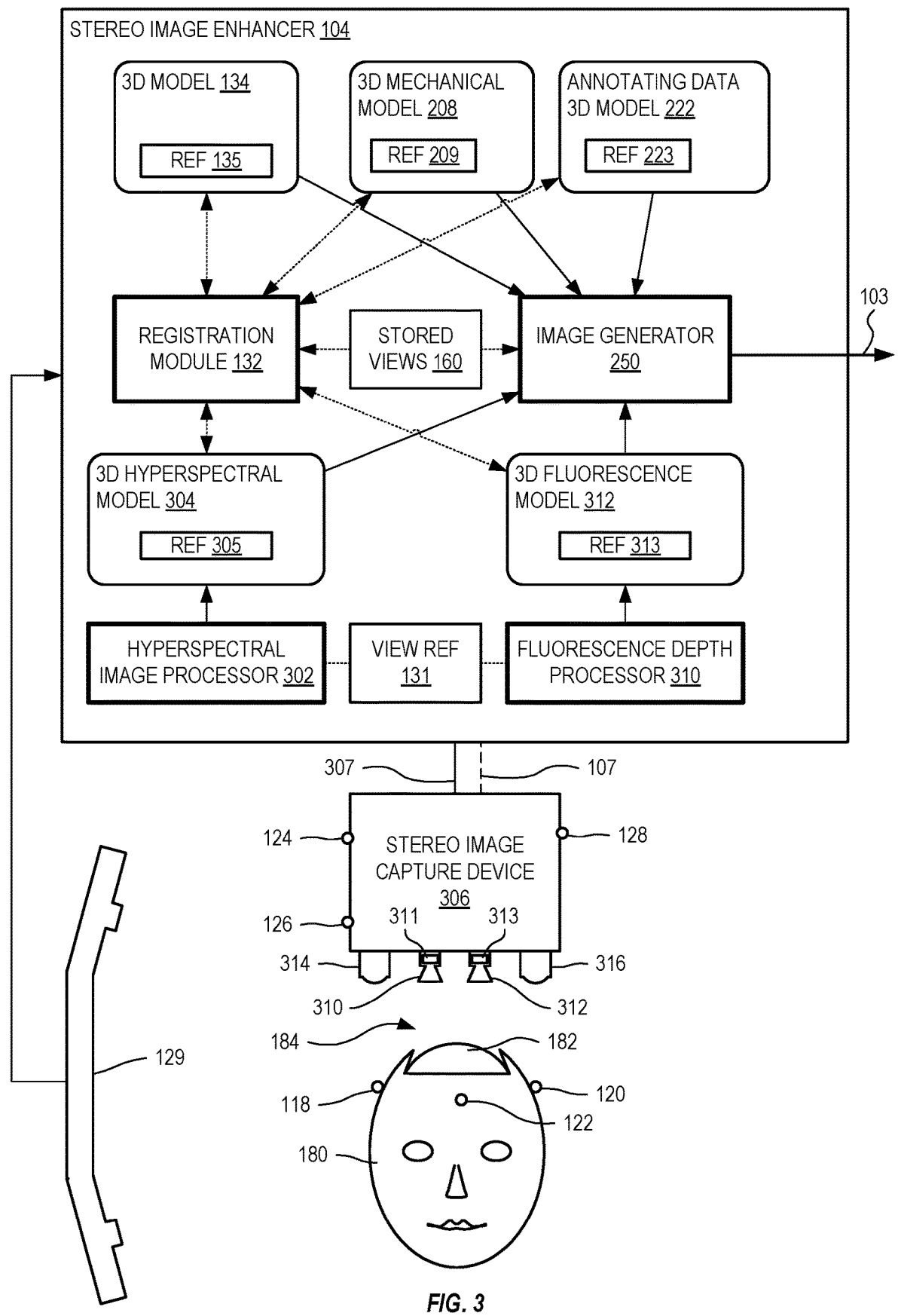
FIG. 3 shows a portion of the stereo imaging system of FIG. 1 configured with stereo hyperspectral cameras for capturing a stereo hyperspectral image stream, in an embodiment.

FIG. 3 shows a portion of stereo imaging system 100 of FIG. 1 configured with stereo hyperspectral cameras 310, 312 for capturing a stereo hyperspectral image stream 307. In a first embodiment, each camera 310, 312 has a monochrome sensor and a controllable color filter 311, 313, wherein the filter is controlled to selectively capture images of a particular color band. In a second embodiment, each camera 310, 312 has a high resolution sensor that is fitted with pattered filters having a plurality (e.g., 64) of color bands, wherein the camera simultaneously captures images in each of the color bands. These cameras operate similarly to conventional color imagers that typically have Bayer filters for separating the captured image into three color bands (red, green, and blue). However, in this embodiment, the image is separated into 64 (or more) distinct color bands (at the expense of resolution). In a third embodiment, each camera 310, 312 has a scanning slit with a dispersing element (e.g., prism or grating) that disperses the image from each point along the slit across multiple pixels of a sensor array, and thereby provides a spectrum, including measurements of intensity at as many as 1024 wavelengths, at each point along the slit. An optical system is configured such that the slit traverses a field of view, and a hyperspectral cube is captured of the entire field of view.

In one embodiment, cameras 310, 312 replace camera 110, 112, wherein processing within stereo image capture device 306 recombines stereo hyperspectral image steam 307 to form stereo image stream 107. In this embodiment, since stereo hyperspectral image stream 307 and stereo image stream 107 are generated from the same captured images, co-registration is ensured.

In another embodiment, cameras 310, 312 are included with cameras 110, 112 such that image streams 107 and 307 are generated independently.

Within enhancer 104, a hyperspectral image processor 302 receives stereo hyperspectral image stream 307 and generates a 3D hyperspectral model 304 with a reference 305. Fluorescence depth processor 310 operates to generate a 3D fluorescence model 312 with a reference 313 from hyperspectral stream 307; in an embodiment fluorescence depth processor 310 determines depth in tissue of fluorophores of 3D fluorescence model 312 by determining observed fluorescent emissions spectra—the intensity of observed fluorescent emissions in hyperspectral stream 307 at two or more wavelengths. The depth processor 310 models spectral shift due to absorption and scattering of light by tissue at those two or more wavelengths relative to known emissions spectra of the fluorophores. Since each fluorophore emits light with a known emissions spectra or distribution of intensity of emitted light at the two or more wavelengths, and tissue absorbs and scatters light at each wavelength differently, deeper fluorophores generally have a greater spectral shift between observed fluorescent emissions spectra and the known emissions spectra of the fluorophores.

Registration module 132 operates to co-register two or more models 134, 208, 222, 304, and 312, and image generator 205 operates to graphically combine at least part of one or more models 134, 208, 222, 304, and 312 with stereo image stream 107 to form enhanced stereo image stream 103. In an embodiment, hyperspectral image processor 302 also is adapted to capture a first fluorescent image and a second fluorescent image at different wavelengths and to produce a third or difference image according to a formula (third image)=K1 (K2*(first image)−(second image)) for some real numbers K1 and K2. In an alternative embodiment, a decay rate image is generated by fitting intensity I of pixels of a sequence of N fluorescent images indexed by integer k taken over a period of time T are fitted to an exponential decay function $I(k)=I(1)10^{-kTd}$, where I(1) is an initial intensity after a fluorescent agent is administered, and d is a per-pixel decay rate;

Captured hyperspectral/fluorescent image streams, and/or determined 3D models therefrom, may be stored for use as annotating data 108 in a following procedure/operation. For example, a first part of a surgical procedure may collect hyperspectral/fluorescence data from a patient, wherein that data is stored within system 100 and used (e.g., as annotating data 108) within a subsequent part of the procedure.

Figure 4:
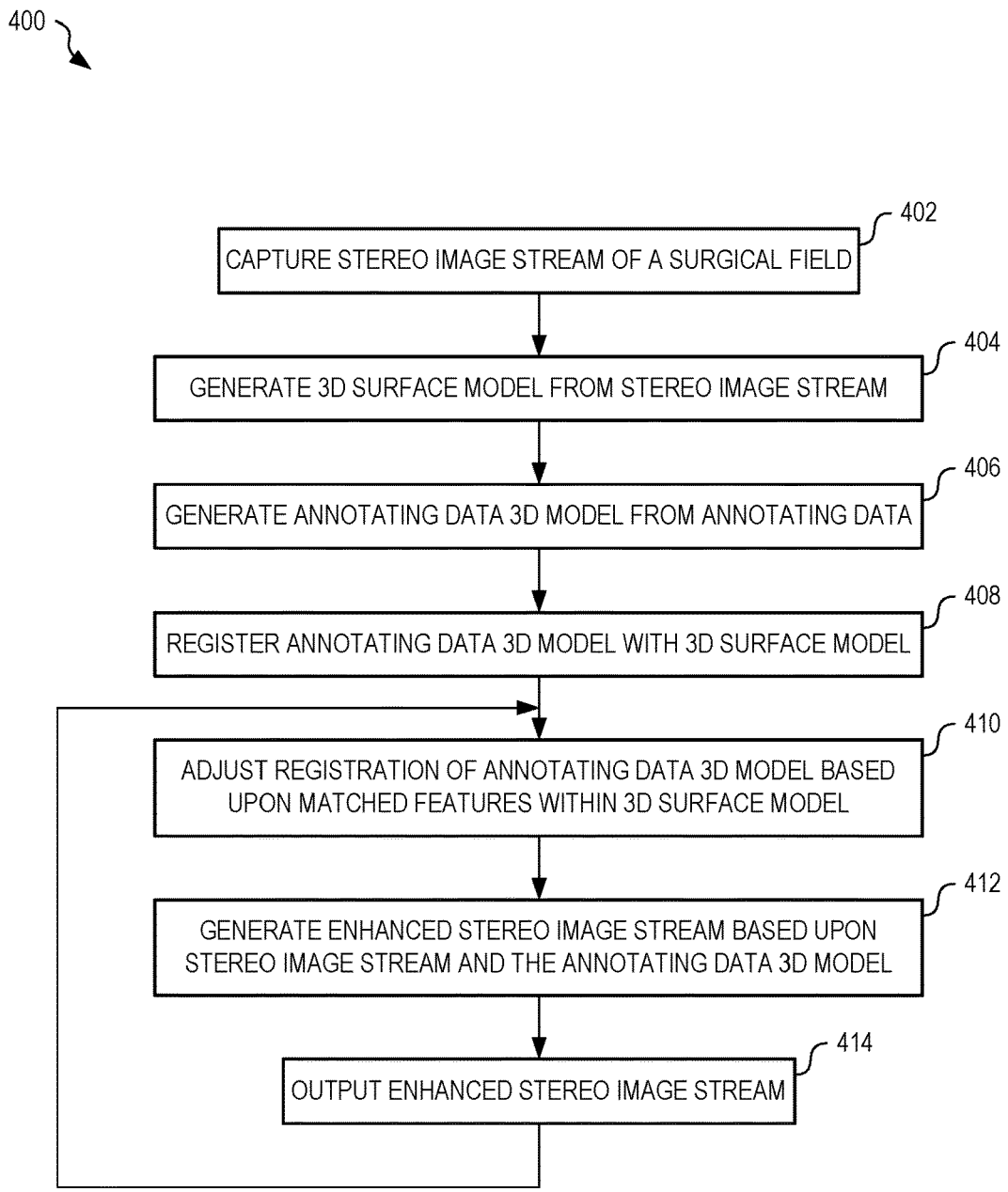
FIG. 4 is a flowchart illustrating one exemplary method for surgical navigation with stereo vision, in an embodiment.

FIG. 4 is a flowchart illustrating one exemplary method 400 for surgical navigation with stereo vision, in an embodiment. In step 402, method 400 captures a stereo image stream of a surgical field. In one example of step 402, stereo image capture device 106 captures stereo image stream 107 of surgical field 184. In step 404, method 400 generates a 3D surface model from the stereo image stream. In one example of step 404, stereo image to 3D surface module 130 generates 3D model 134 based upon stereo image stream 107. In step 406, method 400 generates a 3D enhancing model from annotating data. In one example of step 406, annotating data 3D model generator 220 generates annotating data 3D model 222 from annotating data 108.

In step 408, method 400 registers the 3D enhancing model with the 3D surface model. In one example of step 408, registration module 132 aligns annotating data 3D model 222 with 3D model 134 based upon reference 223 of model 222 and reference 135 of model 134. In step 410, method 400 adjusts registration of the 3D enhancing model based upon matched features between the 3D enhancing model and the 3D surface model; in an embodiment features are matched between these 3D models by manual tagging, in an alternate embodiment common features of the models are matched automatically. In one example of step 410, alignment refiner 202 is invoked by registration model 132 to better register/align identifiable features within annotating data 108 to corresponding features within 3D model 134. In another example of step 410, alignment refiner 202 invokes deformation modeler 206 to annotate a 3D mechanical model 208 with annotating data 108 and then deform 3D mechanical model 208 based upon alignment of corresponding identified features of 3D model 134 to determine post-deformation locations of features found in annotating data 108. Alignment refiner 202 then invokes shifting/rotating/scaling/warping module 204 to apply the identified changes of 3D mechanical model 208 to annotating data 3D model 222.

In step 412, method 400 generates an enhanced stereo image stream based upon the stereo image stream and the annotating data 3D model. In one example of step 412, image generator 250 generates enhanced image stream 103 based upon stereo image stream 107 and at least part of enhanced data 3D model 222.

In step 414, method 400 outputs the enhanced stereo image stream. In one example of step 414, image generator 250 outputs enhanced stereo image stream 103 to stereo viewer 102.

FIG. 5 shows examples of annotating data 108 of FIG. 1. As noted above, annotating data 108 is a previously created set of data from one of radiological studies and physiological studies of the patient. Each data set may be independently modeled by generator 220 to generate an independent annotating data 3D model 222 that may be included at least in part within enhanced stereo image stream 103.

In addition to live hyperspectral, fluorescence depth-resolved, differential fluorescence, and other images, annotating data 108 may include one or more of: a recorded hyperspectral image stream 502 that has an associated reference 503, a recorded fluorescence image stream 504 that has an associated reference 505, a recorded fluorescence difference image stream, a recorded hyperspectral image model 506 that has an associated reference 507, a recorded fluorescence image model 508 that has an associated reference 509, a recorded stereo image stream 510 that has an associated reference 511, a recorded 3D model 512 that has an associated reference 513, MRI data 514 that has an associated reference 515, an fMRI image 516 that has an associated reference 517, a CT image 518 that has an associated reference 519, a single-photon emission computed tomography (SPECT) image 520 that has an associated reference 521, a PET image 522 that has an associated reference 523, an EEG data set 524 that has an associated reference 525, an evoked potentials data set 526 that has an associated reference 527, and a MEG (Magnetoencephalographic) data set 528 that has an associated reference 529. For each data set or image, the associated reference relates the data to the patient-centered coordinate system such that system 100 may relate one set of data with another, and each set of data with 3D model 134.

Figures 6A, 6B:
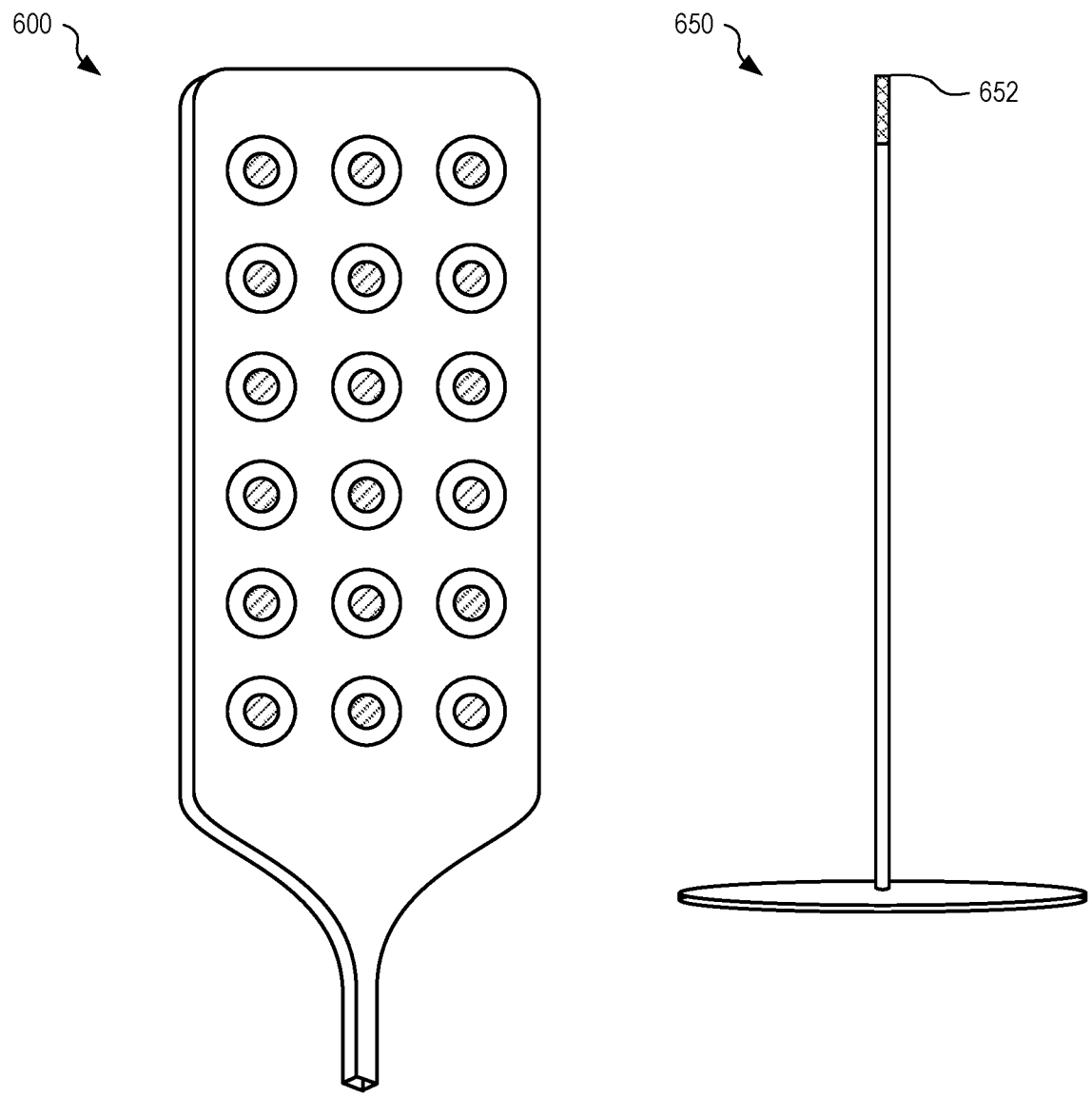
FIG. 6A is a perspective view of one exemplary implantable device model that is stored within the system of FIG. 1, in an embodiment.
FIG. 6B is a perspective view of one exemplary implantable device model that is stored within the system of FIG. 1 in an embodiment.

FIG. 6A shows a perspective view of one exemplary implantable device model 600 that is stored within system 100. Model 600 represents an electrode array that may be implanted subdural, where positioning of the device during surgery is critical to successful operation.

FIG. 6B shows a perspective view of a model 650 of one exemplary implantable device model 650 that is stored within system 100. Model 650 represents a deep brain probe, deep brain stimulator, electrode array, or other device, that should be inserted into a brain such that a tip 652 of the probe is positioned within a target area of the brain. Positioning of the device during surgery is critical to successful operation and is further complicated in that a surgeon is unable to visually see the location of tip 652 with respect to the target area. A current position of the implantable device is determined by triangulation in the 3D images taken by the 3D imaging device using reference marks on the rear or top of the implantable device and known positions of the 3D imaging device.

In an embodiment, during surgery, and in order to facilitate accurate placement of implantable devices, probes, or similar tools, a current 3D model of tissue is rendered and displayed. The current 3D model is displayable from either the point of view of a tip of the implantable device, or from a point of view of a surgeon with a representation of the implantable device, including a representation of portions of the device that are hidden from view by tissue. The system provides for superimposition of modeled locations, as displaced during surgery, of features extracted from annotating data, including a target area for the probe tip in the brain. A surgeon viewing the target area from the point of view of the probe tip can aim the probe at the target area, and by viewing the probe and target area as viewed from a different angle, can judge how much further the probe should be inserted to reach the target area.

Figure 7:
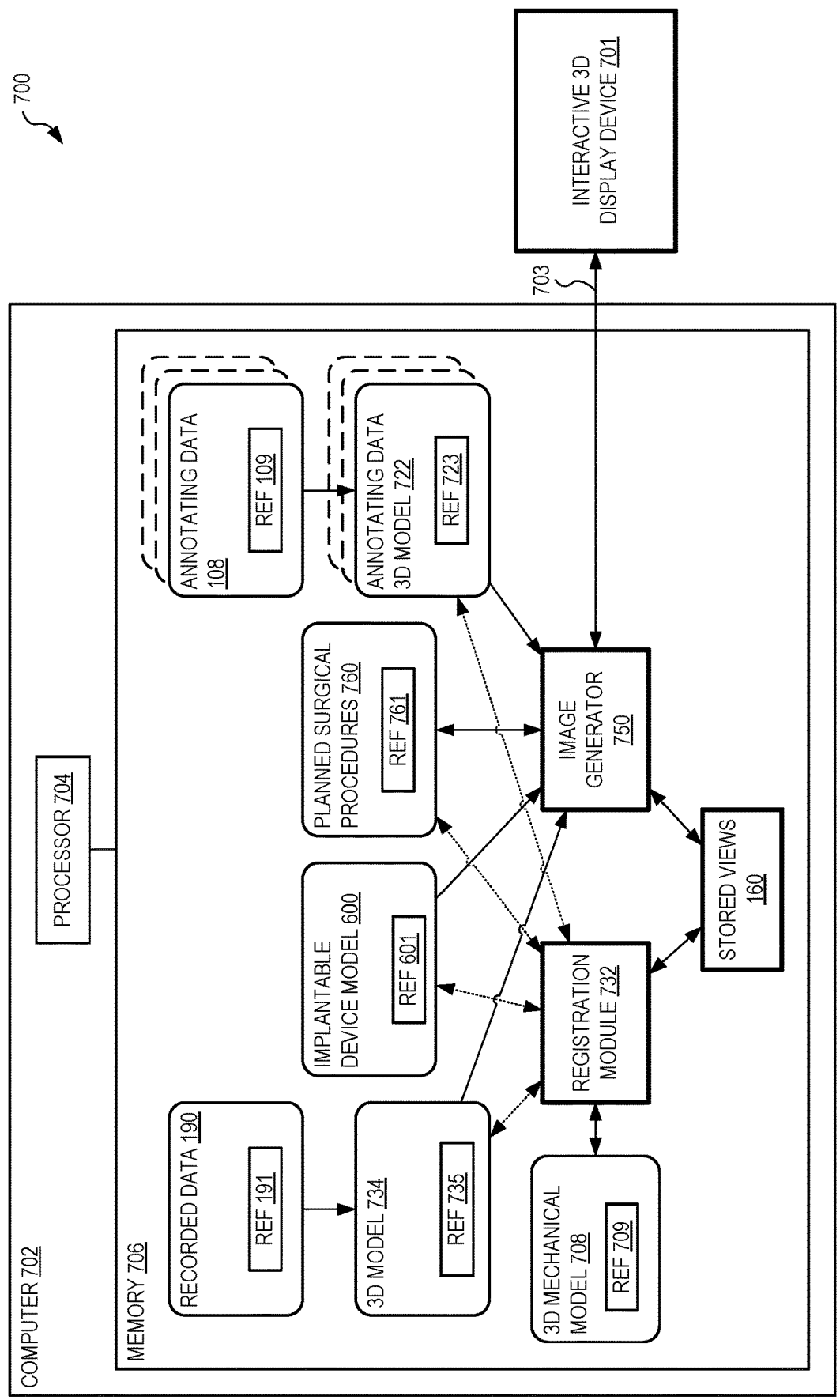
FIG. 7 shows one exemplary system with an interactive stereo display device for interacting with a surgeon to analyze and/or create a surgical procedure for a patient, in an embodiment.

FIG. 7 shows one exemplary system 700 with an interactive stereo display device 701 (e.g., stereo viewer 102 of FIG. 1, a 3D television type display (for use with 3D glasses), touch screen, keyboard and mouse, and so on) for interacting with a surgeon to analyze and/or create a surgical procedure for a patient. In some embodiments, system 700 is used outside of an operating theater to plan a surgical procedure using 3D models of the patient. Recorded data 190 from a previous surgery and/or annotating data 108 captured during a previous procedure on the patient are co-registered and presented for interaction with the surgeon. System 700 has a computer 702 with a processor 704 that is communicatively coupled with a memory 706. Memory 706 is shown storing s registration module 732 and an image generator 750. Registration module 732 and image generator 750 have similar functionality to registration module 132 and image generator 250 of system 100, FIGS. 1 and 2. Registration module 732 and image generator 750 are at least partly implemented as machine readable instructions that are loaded and executed by processor 704 to perform the functionality described herein. Registration module 732 co-registers two or more models to present a coherent stereovision display, that, if desired by the surgeon, shows features of derived from multiple preoperative imaging modalities such as MRI, CT, and ultrasound imaging to a surgeon using system 700.

The surgeon interacts with interactive 3D display device 701 to manipulate models of one or more of an implantable device, define planned surgical procedures 760, and define views within stored views 160 for use during a procedure. For example, system 700 allows a surgeon to plan an operation by manipulating views (e.g., rendered images that may include appropriate shading and simulated lighting) of one or more 3D models 734, 600, 722, defining the planned surgical procedures 760, such as making incisions, positioning an implantable device, and preselecting the appropriate views (stored within stored views 160) of annotating data 108 to support the operation.

In one example of operation, the surgeon positions a model of an implantable device relative to a 3D model of a patient's brain generated from MRI data. The surgeon defines one or more views of the modeled implant and modelled MRI data (and any other annotating data 108 that may provide useful information) that will provide additional guidance to the surgeon during the operation. Implantable device model 600, planned surgical procedures 760, and stored views 160 are then used within system 100 to provide additional support to the surgeon during the operation.

In another example of operation, the surgeon selects previously recorded data 190 and annotating data 108 for a patient and operates system 700 to generate a view of at least a portion of the patient based upon an indicated surgical field (e.g., surgical field 184, FIG. 1). The surgeon may adjust the field of view to synchronously rotate the viewed image. Thus, the surgeon may select a stereo view of the models that is optimal for positioning an implantable device, or for planning a surgical procedure. Registration module 732 aligns (co-registers) a 3D model 734 generated from recorded data 190 with an annotating data 3D model 722 generated from annotating data 108 such that the generated view of 3D model 734 and annotating data 3D model 722 are consistent. For example, where annotating data 3D model 722 is based upon MRI tomographic images, the surgeon may select a particular cross section or portion of annotating data 3D model 722 for display within stereo viewer 102 during the operation.

As with system 100, registration module 732 aligns 3D model 734 and annotating data 3D model 722 based upon reference 735 and reference 723, respectively. Registration module 732 may also include an alignment refiner (similar to alignment refiner 202, FIG. 2) to ensure correct alignment of 3D model 722 with 3D model 734.

Planned surgical procedures 760 define surgical activities that the surgeon intends to perform on the patient. These activities are selected from the group including resection, retraction, trajectory determination, and surgical corridor, and may be defined singly or in combination. These surgical activities are thus defined preoperatively with respect to one or more imaging data sets previously captured of the patient.

System 700 may include a 3D mechanical model 708 (similar to 3D mechanical model 208 of FIG. 2) that is used to model tissue in at least part of the surgical field and/or annotating data 3D model 722 such that tissue displacement resulting from planned surgical procedures 760 are predicted and portrayed correctly.

Figure 8:
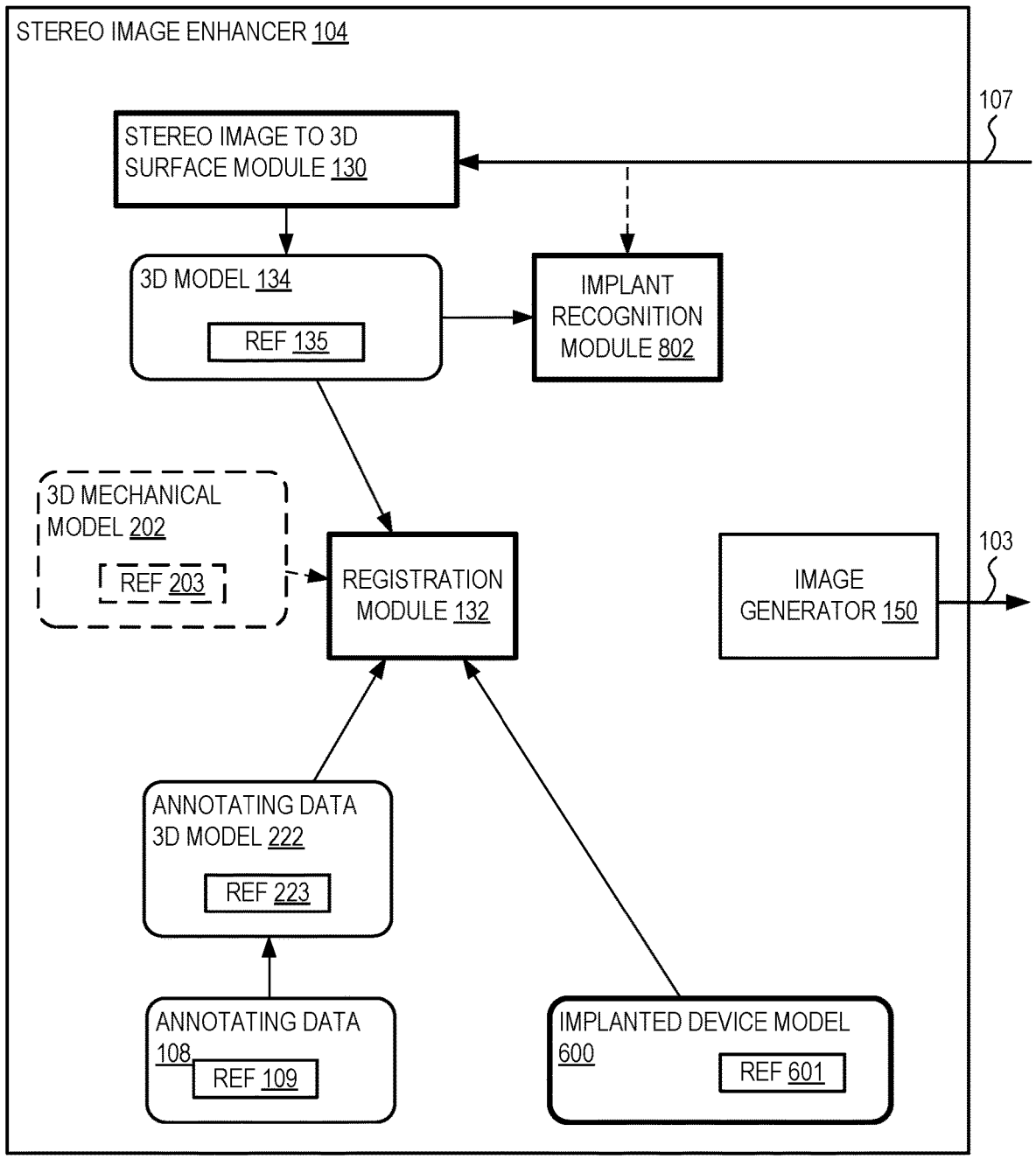
FIG. 8 shows the system of FIG. 1 further configured for use in positioning an implantable device during a surgical procedure, in an embodiment.

FIG. 8 shows system 100 of FIG. 1 further configured for use in positioning an implantable device during a surgical procedure based upon implantable device model 600 and associated reference 601, where reference 601 is defined by system 700 of FIG. 7 as the intended position of the implantable device within the patient.

As previously described, system 100 invokes stereo image to 3D surface module 130 to generate 3D model 134 based upon stereo image stream 107. Registration module 132 then aligns (co-registers) annotating data 3D model 122 and implantable device model 600 with 3D model 134 based upon references 123, 601, and 135. System 100 may then refine this alignment using alignment refiner 202 (not shown in FIG. 8) as described above.

System 100 may also include an implant recognition module 802 that operates to detect the location of an implant within 3D image stream 107 based upon implanted device model 600. Implant recognition module 802 may determine position and orientation of the implant even when only a part of the implant is visible within stereo image stream 107. In one embodiment, the implant includes identification and orientation markings that aid recognition and orientation by implant recognition module 802.

By determining position and orientation of the implantable device and the desired position of the implantable device, system 100 may generate graphical guides to aid the surgeon's positioning and insertion of the device. In particular, by modeling deformation of tissues (including target and other non-visible structures) resulting from applied pressure and/or displacement, system 100 provides guidance for more accurate positioning of the implantable devices as compared to using conventional placement means. Further, where the implantable device passes adjacent critical structures within the tissue, system 100 may provide warnings (visual and/or audio) to the surgeon where the device is approaching such critical areas. Visual indications may include 3D graphical display of target and critical structures and a 3d graphical representation of the implantable device as it moves through the tissue during the procedure.

As shown in FIG. 1, system 100 may record one or both of stereo image stream 107 and enhanced stereo image steam 107 throughout the surgical procedure/operation. System 700 of FIG. 7 may they be used to perform a post-operative analysis of the surgical procedure based upon the recorded information and annotating data 108, wherein system 700 automatically refines alignment and uses 3D mechanical model 702 to allow for tissue deformation resulting from activities during the operational procedure. Recorded data 190 thereby provide documentation of the surgical procedure for future reference and analysis alone or co-registered with other imaging data sets of annotating data 108, even where the annotating data 108 was not used during the surgery—such as when obtained post-surgery.

Recorded data 190 and annotating data 108 may be used for postoperative use of intraoperatively acquired functional information (including but not limited to motor, sensory, speech, memory, and other cognitive function). For example, recorded data 190 may be co-registered with other annotating data 108 acquired postoperatively.

Recorded data 190 (e.g., hyperspectral stereo imaging data) and annotating data 108 may be used to determine abnormal tissue physiological properties, including but limited to blood flow and tissue oxygenation, and to concentrations of selective and nonselective fluorescent optical biomarkers.

Recorded data 190 may be analyzed using system 700 together with subsequently acquired and potentially co-registered imaging data sets, either extraoperatively or intraoperatively at any subsequent surgery.

Figure 10A:
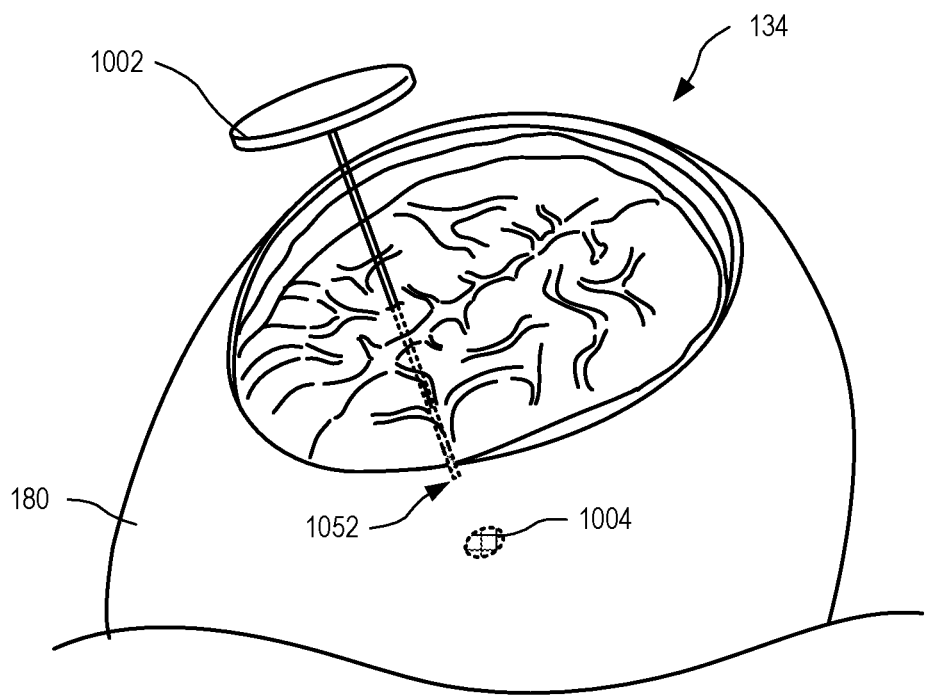
FIG. 10A is a perspective view of the 3D model of FIG. 1 and the implantable device model of FIG. 6B.
Figure 10B:
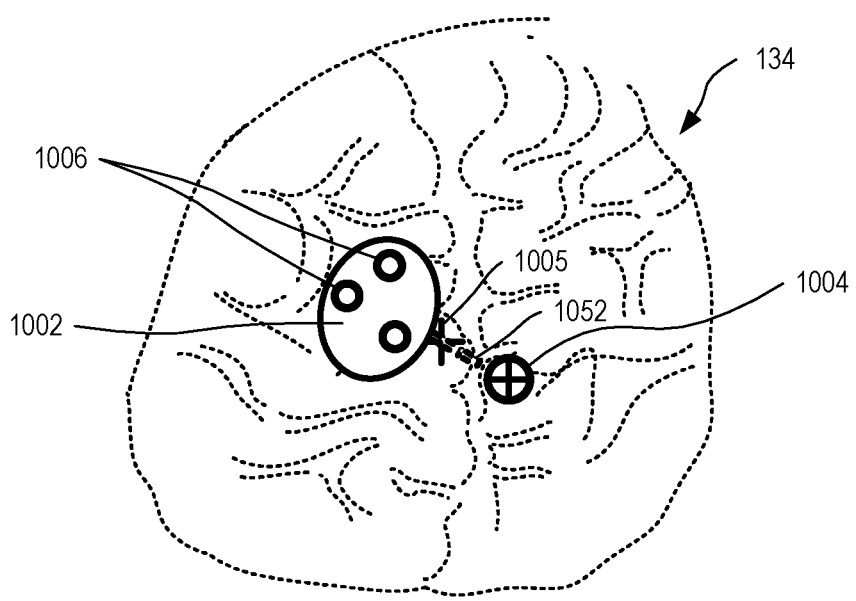
FIG. 10B is a 2D representation of the enhanced stereo image stream of the surgical field corresponding to FIG. 10A as generated by the system of FIG. 1.

FIG. 10A is a perspective view of 3D model 134 and implantable device model 650 illustrating a tip 1000 of a partially positioned device corresponding to model 650 in relation to a target area 1004 within brain 182. FIG. 10B is a 2D representation of enhanced stereo image stream 103 (i.e., the surgeon's view) of surgical field 184 corresponding to FIG. 10A. As appreciated, the 3D view resulting from enhanced stereo image stream 103 provides significantly more information that can be shown in the 2D example of FIG. 10B. FIGS. 10A and 10B are best viewed together with the following description.

The position and orientation of the device being implanted is detected by implant recognition module 802 and model 650 positioned relative to 3D model 134 accordingly. Target area 1004 is defined within planned surgical procedures 760 for example, and may include a desired entry point 1005 and/or path for the implantable device. A view of models 134, 650 and target area 1004 is generated corresponding to the surgeon's view of surgical area 184 and added to enhanced stereo image stream 103 such that the surgeon sees, in 3D, a representation 1052 (e.g., a rendered image) of tip 652 and target area 1004 in relation to surgical field 184. The surgeon may also view models 134, 650 and target area 1004 from other perspectives during the activity of inserting the implantable device. Since the position of the device being implanted is determined from stereo image stream 107 and is accurately co-registered (aligned) with the tissue of patient 180 based upon 3d model 134, the displayed alternate view is also accurate and updated in real-time. Implantable device 1002 may have one or more visibly detectable markings to facilitate determining orientation of device 1002 by implant recognition module 802.

Figure 11:
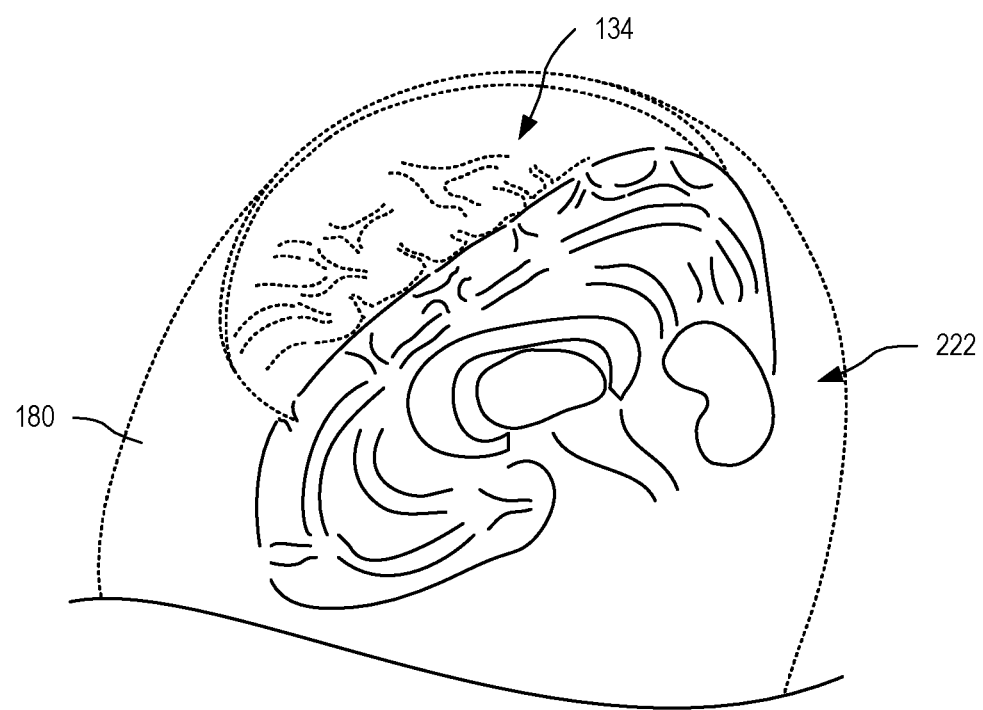
FIG. 11 is a perspective view of the 3D model and the annotating data 3D model generated from the annotating data of FIG. 1, where the annotating data is based upon MRI tomography data.

Other annotating data 108 may also be selected for display to the surgeon. FIG. 11 is a perspective view of 3D model 134 and annotating data 3D model 222 generated from annotating data 108 based upon MRI tomography data. For clarity of illustration, model 650 and target area 1004 are not shown in the example of FIG. 11, but could be selectively added by the surgeon to show progress of tip 652 towards target area 1004.

In the example of FIG. 11, a section of annotating data 3D model 222 is superimposed onto a cut-away of 3D model 134 to emphasize the inner structures of tissue below the surface of 3D model 134. System 100 generates enhanced stereo image stream 103 to superimpose the hidden tissue structure onto the surgeon's view of surgical field 184. Since model 222 is aligned with 3d model 134 and corrected based upon 3D mechanical model 208, system 100 enhances the surgeons view with a very accurate 3D portrayal of the tissue normally hidden from the surgeon's view.

Figure 9:
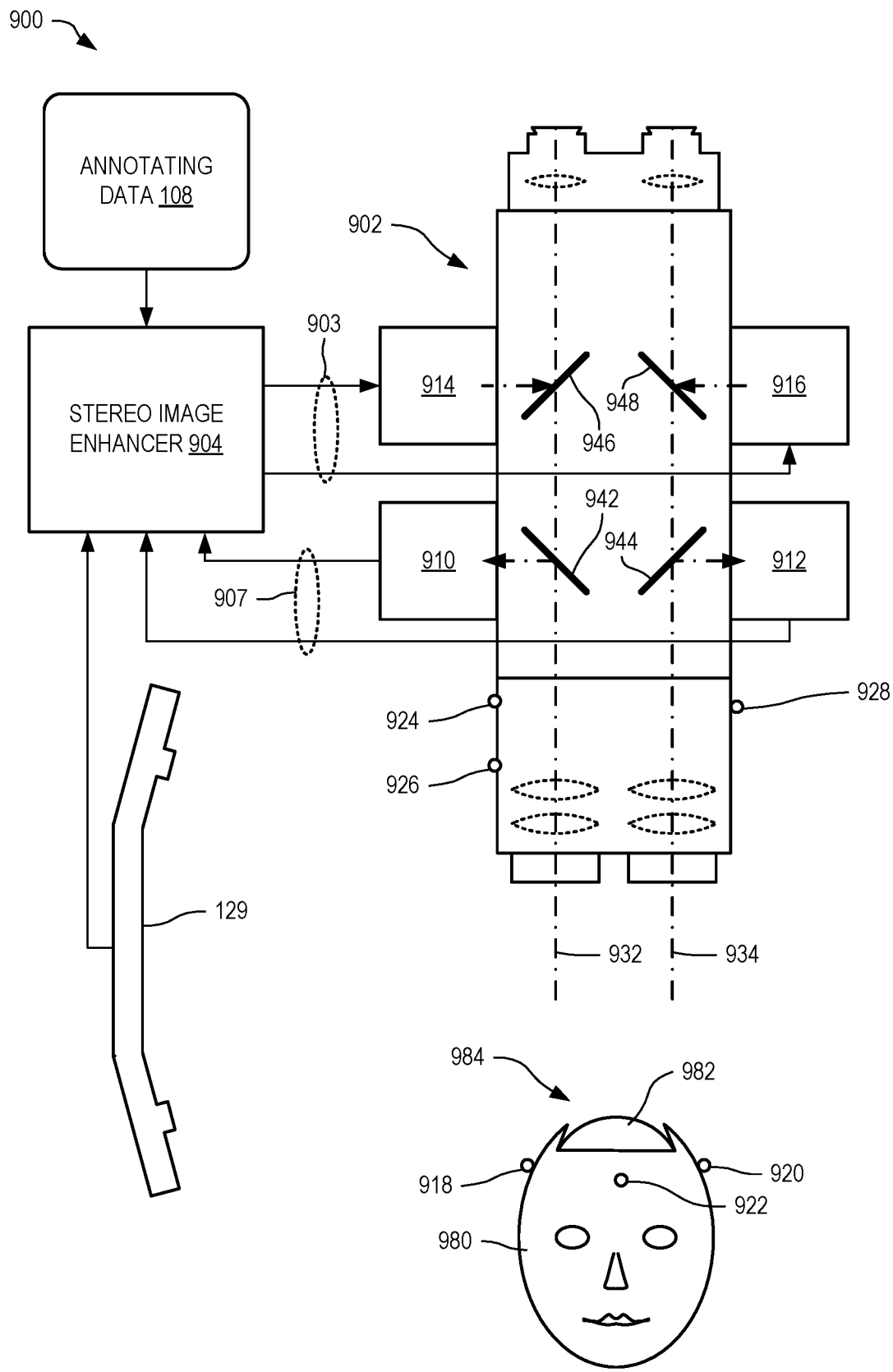
FIG. 9 shows one exemplary optical system for surgical navigation with stereovision, in an embodiment.

FIG. 9 shows one exemplary system 900 for surgical navigation with stereovision. System 900 includes an optical surgical microscope 902 and a stereo image enhancer 904 that receives a stereo image stream 907 of a surgical field 984 from cameras 910 and 912. System 900 operates similarly to system 100 of FIG. 1 to enhance a surgeon's view of a surgical field 984.

At least three reference points 918, 920, 922 may be attached to patient 980 for the duration of the procedure and the location of each reference point is defined as a location within a patent-centered coordinate system of patient 980. As with system 100, tracker 129 determines locations of reference points 918, 920, 922 attached to patient 980 and reference points 924, 926, 928 attached to microscope 902. Stereo image enhancer 904 uses these locations to determine a view reference (e.g., spatial relationship including relative position and orientation) between patient 980 and microscope 902 to define a reference of stereo image stream 907 captured by cameras 910, 912. Stereo image enhancer 904 generates and sends an enhancing image stream 903 to image projectors 914, 916 that project the images from stereo image stream 903 into optical paths 932, 934, respectively. As shown, optical path 932 includes a first beam splitter 942 that diverts a portion of light from surgical field 984 to camera 910 and a beam combiner 946 that adds light from image projector 914 to optical path 932. Similarly, optical path 934 includes a first beam splitter 944 that diverts a portion of light from surgical field 984 to camera 912 and a beam combiner 948 that adds light from image projector 916 to optical path 934.

Combinations

The features and capabilities herein described may be combined in many different ways into a system; for example but not limitation the fluorescent depth processor and fluorescent stimulus light sources may be in an optional, extra-cost, module found in some systems but not in others. Among other combinations of features anticipated include:

A system designated A for generating a photographic image of a surgical field, including a stereo image capture device for capturing a stereo image stream from two cameras imaging the surgical field; and a stereo viewer for displaying the stereo image stream to a surgeon. The system also includes a stereo image to 3D surface extraction module, implemented as machine readable instructions stored in memory of a computer, that is capable of, when the instructions are executed by a processor of the computer, generating a first 3D model of the surgical field from the stereo image streams; a registration module, implemented as machine readable instructions stored in the memory, that is capable of, when the instructions are executed by the processor, co-registering annotating data with the first 3D model; and a stereo image enhancer, implemented as machine readable instructions stored in the memory, that is capable of, when the instructions are executed by the processor, graphically overlaying at least part of the annotating data onto the stereo image stream to form an enhanced stereo image stream for display by the stereo viewer, wherein the enhanced stereo stream enhances the surgeon's perception of the surgical field.

A system designated AA including the system designated A, wherein the registration module aligns the annotating data with the first 3D model.

A system designated AB including the system designated A or AA further including a 3D model generator for generating a second 3D model from the annotating data, wherein the registration module co-registers the second 3D model with the first 3D model; and an image generator configured to generate a graphical image of the second 3D model based upon the surgical field.

A system designated AC including the system designated A, AA or AB wherein the annotating data comprises one of a preoperative, an intraoperative and a postoperative radiological study selected from the group consisting of magnetic resonance imaging (MRI), functional magnetic resonance imaging (fMRI), x-ray computed tomography (CT), Single-photon emission computed tomography (SPECT), and positron emission tomography (PET).

A system designated AD including the system designated AB or AC, the image generator configured to generate a cross sectional view of the second 3D model based upon an indicated surgical plane within the surgical field.

A system designated AE including the system designated A, AA, AB, AC, or AD wherein the annotating data further comprises physiological study data selected from the group including EEG, evoked potentials, and magnetoencephalography (MEG).

A system designated AF including the system designated A, AA, AB, AC, AD or AE, the registration module further including an alignment refiner configured to adjust the registration of the annotating data with the 3D model based upon matching of features within the 3D model and features within the annotating data.

A system designated AF including the system designated A, AA, AB, AC, AD, AE, or AF, the registration module further including a deformation modeler configured to deform the annotating data based upon a determined tissue deformation within the surgical field.

A system designated AG including the system designated AF, the tissue deformation resulting from one or more of skull removal, retraction, and incision.

A system designated AH including the system designated A, AA, AB, AC, AD, AE, AF, or AG and further including a first controllable filter coupled with a first of the two cameras to filter light entering the first of the two cameras from the surgical field; a first controllable light source for illuminating the surgical field with light of a determined fluorescent stimulus wavelength; and a fluorescence depth processor, implemented as machine readable instructions stored in the memory, that is capable of, when the instructions are executed by the processor, generating a 3D fluorescence model; wherein the stereo image enhancer graphically overlays at least a portion of the 3D fluorescence model onto the enhanced stereo image stream.

A system designated AK including the system designated AH, further including a second controllable filter coupled with a second of the two cameras to filter light entering the second of the two cameras from the surgical field; and a hyperspectral image processor, implemented as machine readable instructions stored in the memory, that is capable of, when the instructions are executed by the processor, controlling the first and second filters to capture a stereo hyperspectral image stream and generate a 3D hyperspectral model; wherein the stereo image enhancer graphically overlays at least a portion of the 3D hyperspectral model onto the enhanced stereo image stream.

A system designated AL including the system designated A, AA, AB, AC, AD, AE, AF, or AG, further including a first and a second hyperspectral imaging camera for capturing a stereo hyperspectral image stream of the surgical field; and a hyperspectral image processor, implemented as machine readable instructions stored in the memory, that is capable of, when the instructions are executed by the processor, generating a 3D hyperspectral model from the stereo hyperspectral image stream; wherein the stereo image enhancer graphically overlays at least a portion of the 3D hyperspectral model onto the enhanced stereo image stream.

A system designated B for graphically representing and displaying a first and second annotating data in relation to a surgical field, including an interactive display device; a registration module, implemented as machine readable instruction stored in a memory of a computer, that is capable of, when the instructions are executed by a processor of the computer, co-registering the first and second annotating data; and a stereo image enhancer, implemented as machine readable instruction stored in the memory, that is capable of, when the instructions are executed by the processor, graphically overlaying at least part of the annotating data onto the stereo image stream to form an enhanced stereo image stream for display by the stereo viewer, wherein the enhanced stereo stream enhances the surgeon's perception of the surgical field.

A system designated BA including the system designated B, further configured to review a recorded surgical procedure that is co-registered with post operatively acquired imaging and/or physiological data.

A method designated C for surgical navigation with stereo vision, including capturing a stereo image pair of a surgical field; generating a 3D surface model from the stereo image pair; registering preoperatively captured annotating data with the 3D surface model; generating an enhanced stereo image based upon the stereo image pair and the annotating data; wherein the annotating data is graphically overlaid onto the stereo image pair.

A method designated CA including the method designated C, the step of registering further including generating a 3D model based upon the annotating data; and registering the 3D model to the 3D surface model.

A method designated CB including the method designated C or CA, further including adjusting the annotating data based upon matched features of the 3D surface model and features of the annotating data.

A method designated CC including the method designated C, CA, or CB, the step of adjusting comprising one or more of shifting, rotating, warping, and scaling the annotating data.

A method designated CD including the method designated C or CA, the step of adjusting including generating a mechanical model of the tissue within the surgical field to determine the adjustment of the enhanced data.

A method designated CE including the method designated C, CA, CB, or CC, further including recording the stereo image pair.

A method designated CF including the method designated C, CA, CB, or CC, further including recording the enhanced stereo image pair.

A method designated CG including the method designated C, CA, CB, or CC, wherein the annotating data comprises one of a preoperative, an intraoperative and a postoperative radiological study selected from the group consisting of magnetic resonance imaging (MRI), functional magnetic resonance imaging (fMRI), x-ray computed tomography (CT), Single-photon emission computed tomography (SPECT), and positron emission tomography (PET).

A method designated CH including the method designated C, CA, CB, CC, CD, CE, CF, or CG, wherein the annotating data further comprises a physiological study selected from the group including EEG, evoked potentials, and magnetoencephalography (MEG).

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A system for generating a photographic image of a surgical field, comprising:
    a stereo image capture device for capturing a stereo image stream from two optical cameras imaging the surgical field during a surgical procedure;
    a stereo viewer for displaying the stereo image stream to a surgeon;
    a stereo image to 3D surface model extraction module, implemented as machine readable instructions stored in memory of a computer, adapted to, when the instructions are executed by a processor of the computer, generate a first 3D model of the surgical field from the stereo image stream;
    a registration module, implemented as machine readable instructions stored in the memory, adapted to, when the instructions are executed by a processor of the computer, co-register annotating data with the first 3D model; and
    a stereo image enhancer, implemented as machine readable instructions stored in the memory, adapted to, when the instructions are executed by a processor of the computer, graphically overlay at least part of the annotating data onto the stereo image stream to form an enhanced stereo image stream for display by the stereo viewer, wherein the enhanced stereo stream enhances the surgeon's perception of the surgical field,
    wherein the registration module automatically determines spatial relationship between the 3D model and features of patient bone structure from preoperative scans and determines if there is an inconsistency, and if an inconsistency is found generates a warning.

2. The system of claim 1 wherein the annotating data comprises images representing planned surgical procedures.

3. The system of claim 2 wherein the images representing planned surgical procedures are rendered images from a 3D model adapted to represent tissue as deformed during surgery.

4. The system of claim 2 wherein the annotating data comprises images representing implantable devices.

5. The system of claim 4 further comprising a recognition module adapted to recognize an implantable device.

6. The system of claim 5 wherein the adjusting of annotating data comprises adjustment for tissue deformation due to presence of the implantable device.

7. The system of claim 5 wherein the implantable device is selected from the group consisting of a of a deep-brain probe, deep-brain stimulator, and a subdural electrode array.

8. The system of claim 7 wherein the annotating information is derived from at least one of preoperative imaging with an imaging method selected from the group consisting of magnetic resonance imaging (MRI), functional magnetic resonance imaging (fMRI), x-ray computed tomography (CT), single-photon emission computed tomography (SPECT), and positron emission tomography (PET), and combined with data from at least one physiological studies selected from the group consisting of electroencephalography (EEG), evoked potentials, and magnetoencephalography (MEG).

9. The system of claim 1 wherein the annotating information is derived from at least one of preoperative imaging with an imaging method selected from the group consisting of magnetic resonance imaging (MRI), functional magnetic resonance imaging (fMRI), x-ray computed tomography (CT), single-photon emission computed tomography (SPECT), and positron emission tomography (PET), and combined with data from at least one physiological studies selected from the group consisting of electroencephalography (EEG), evoked potentials, and magnetoencephalography (MEG).

10. A method for surgical navigation with stereo vision, comprising:
    capturing a stereo image pair of a surgical field during an operation on the surgical field;
    generating a 3D surface model from the stereo image pair;
    registering annotating data with the 3D surface model, said registering including adjusting the annotating data based upon matched features of the 3D surface model and features of the annotating data, said adjusting including generating a mechanical model of the tissue within the surgical field;

generating an alarm if inconsistency between bony features of the annotating data are inconsistent with features extracted from the 3D surface model;
generating an enhanced stereo image based upon the stereo image pair and the annotating data as registered with the 3D surface model;
wherein the annotating data is graphically overlaid onto the stereo image pair as registered with the 3D surface.

11. The method of claim 10 wherein the annotating data comprises images representing planned surgical procedures.

12. The method of claim 11 wherein the images representing planned surgical procedures are rendered images from a 3D model adapted to represent tissue as deformed during surgery.

13. The system of claim 11 wherein the annotating data comprises images representing implantable devices.

14. The method of claim 13 further comprising a recognition module adapted to recognize an implantable device.

15. The method of claim 14 wherein the adjusting of annotating data comprises adjustment for tissue deformation due to presence of the implantable device.

16. The method of claim 15 wherein the implantable device is selected from the group consisting of a deep-brain probe, deep-brain stimulator, and a subdural electrode array.

17. The method of claim 16 wherein the annotating information is derived from at least one of preoperative imaging with an imaging method selected from the group consisting of magnetic resonance imaging (MRI), functional magnetic resonance imaging (fMRI), x-ray computed tomography (CT), single-photon emission computed tomography (SPECT), and positron emission tomography (PET), and combined with data from at least one physiological studies selected from the group consisting of electroencephalography (EEG), evoked potentials, and magnetoencephalography (MEG).

18. The method of claim 10 wherein the annotating information is derived from at least one of preoperative imaging with an imaging method selected from the group consisting of magnetic resonance imaging (MRI), functional magnetic resonance imaging (fMRI), x-ray computed tomography (CT), single-photon emission computed tomography (SPECT), and positron emission tomography (PET), and combined with data from at least one physiological studies selected from the group consisting of electroencephalography (EEG), evoked potentials, and magnetoencephalography (MEG).

* * * * *